United States Patent [19]

Fauchere et al.

[11] Patent Number: 5,317,014
[45] Date of Patent: May 31, 1994

[54] PEPTIDES AND PSEUDOPEPTIDES DERIVED FROM TACHYKININ

[75] Inventors: Jean-Luc Fauchere, Saint-Cloud; Nathalie Kucharczyk, Paris; Angela D. Morris, Viroflay; Joseph Paladino, Conflans Sainte Honorine; Jacqueline Bonnet, Paris; Christophe Thurieau, Boulogne sur Seine, all of France

[73] Assignee: Adir et Compagnie, Courbevoie, France

[21] Appl. No.: 893,930

[22] Filed: Jun. 3, 1992

[30] Foreign Application Priority Data

Apr. 6, 1991 [FR] France ................................ 91 06721

[51] Int. Cl.$^5$ ............... A61K 37/02; C07K 5/06; C07K 5/08; C07K 5/10
[52] U.S. Cl. ........................................... 514/17; 514/18; 530/330; 530/331
[58] Field of Search .................. 514/17, 18; 530/330, 530/331

[56] References Cited

U.S. PATENT DOCUMENTS

5,128,447  7/1992  Rovero et al. ................. 530/328
5,164,372 11/1992  Matsuo et al. ................. 514/19

OTHER PUBLICATIONS

Morrison and Boyd, *Organic Chemistry*, 4th ed., pp. 928, 1132 (1983), Allyn and Bacon, Inc.

European J. Biochem 138, 9 (1984) Title: IUPAC-IUB Joint Commission on Biochemical Nomenclature, "Nomenclature and Symbolism for Amino Acids and Peptides".

O. Arunlakshana et al., Brit. J. Pharmacol. 14, 48–58 (1959). Title: "Some Quantitative Uses of Drug Antagonists".

D. Regoli et al., European Journal of Pharmacology 134 321–326 (1986). Title: "The Rat Isolated Portal Vein: A Preparation Sensitive to Neurokinins, Particularly Neurokinin B".

D. Regoli et al., European Journal of Pharmacology 125, 37–44 (1985). Title: "Different Receptors are Involved in the Endothelium-Mediated Relaxation and the Smooth Muscle Contraction of the Rabbit Pulmonary Artery in Response to Substance P and Related Neurokinins".

*Primary Examiner*—Lester L. Lee
*Assistant Examiner*—Carol A. Sabata
*Attorney, Agent, or Firm*—Gordon W. Hueschen

[57] ABSTRACT

A compound of formula (I):

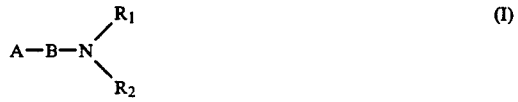

in which:

$R_1$ and $R_2$, which are identical or different, represent hydrogen, or alkyl, cycloalkyl or benzyl, B represents a residue of an aromatic amino acid, A represents a peptide residue comprising from one to three amino acids, in cyclic or linear form, and medicaments containing the same, are disclosed.

9 Claims, No Drawings

SEQUENCE LISTING ( 1 ) GENERAL INFORMATION:

( i i i ) NUMBER OF SEQUENCES: 46

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="Cyclo(Abo-Asp)
        Abo=2- azabicyclo-[2.2.2]octane-3-carbonyl"

( i x ) FEATURE:
        ( A ) NAME/KEY: Modified-site
        ( B ) LOCATION: 3
        ( D ) OTHER INFORMATION: /note="trp(CHO)"

( i x ) FEATURE:
        ( A ) NAME/KEY: Modified-site
        ( B ) LOCATION: 5
        ( D ) OTHER INFORMATION: /note="N(CH3)CH2C6H5"

( x i ) SEQUENCE DESCRIPTION: SEQ ID NO:1:

```
Xaa  Asp  Trp  Phe  Xaa
1                    5
```

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="Cyclo(abo-Asp) see seq id 1"

( i x ) FEATURE:
        ( A ) NAME/KEY: Modified-site
        ( B ) LOCATION: 3
        ( D ) OTHER INFORMATION: /note="trp(CHO)"

( i x ) FEATURE:
        ( A ) NAME/KEY: Modified-site
        ( B ) LOCATION: 5
        ( D ) OTHER INFORMATION: /note="see seq id 1"

( x i ) SEQUENCE DESCRIPTION: SEQ ID NO:2:

```
Xaa  Asp  Trp  Phe  Xaa
1                    5
```

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="Cyclo(Tic-Asp) Tic=1,2,3,4-tetrahydroisoquinoline-3-carbonyl"

( i x ) FEATURE:
        ( A ) NAME/KEY: Modified-site
        ( B ) LOCATION: 3
        ( D ) OTHER INFORMATION: /note="trp(CHO)"

( i x ) FEATURE:
        ( A ) NAME/KEY: Modified-site
        ( B ) LOCATION: 5
        ( D ) OTHER INFORMATION: /note="see seq id 1"

( x i ) SEQUENCE DESCRIPTION: SEQ ID NO:3:

```
Xaa  Asp  Trp  Phe  Xaa
1                    5
```

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="Cyclo(Abo-asp) see seq id

1"

( i x ) FEATURE:
    ( A ) NAME/KEY: Modified-site
    ( B ) LOCATION: 3
    ( D ) OTHER INFORMATION: /note="trp(CHO)"

( i x ) FEATURE:
    ( A ) NAME/KEY: Modified-site
    ( B ) LOCATION: 5
    ( D ) OTHER INFORMATION: /note="seq id 1"

( x i ) SEQUENCE DESCRIPTION: SEQ ID NO:4:

Xaa Asp Trp Phe Xaa
1                 5

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="Cyclo(abo-asp)
            seq id 1"

( i x ) FEATURE:
    ( A ) NAME/KEY: Modified-site
    ( B ) LOCATION: 3
    ( D ) OTHER INFORMATION: /note="trp(CHO)"

( i x ) FEATURE:
    ( A ) NAME/KEY: Modified-site
    ( B ) LOCATION: 5
    ( D ) OTHER INFORMATION: /note="see seq id 1"

( x i ) SEQUENCE DESCRIPTION: SEQ ID NO:5:

Xaa Asp Trp Phe Xaa
1                 5

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="Cyclo(Tic-asp)
            see seq id
            3"

( i x ) FEATURE:
    ( A ) NAME/KEY: Modified-site
    ( B ) LOCATION: 3
    ( D ) OTHER INFORMATION: /note="trp(CHO)"

( i x ) FEATURE:
    ( A ) NAME/KEY: Modified-site
    ( B ) LOCATION: 5
    ( D ) OTHER INFORMATION: /note="see seq id 1"

( x i ) SEQUENCE DESCRIPTION: SEQ ID NO:6:

Xaa Asp Trp Phe Xaa
1                 5

( 2 ) INFORMATION FOR SEQ ID NO:7:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1..2
    (D) OTHER INFORMATION: /note="Cyclo(MePhe-Asp)
        MePhe=methylphenylalanine"

(ix) FEATURE:
    (A) NAME/KEY: Modified-site
    (B) LOCATION: 3
    (D) OTHER INFORMATION: /note="trp(CHO)"

(ix) FEATURE:
    (A) NAME/KEY: Modified-site
    (B) LOCATION: 5
    (D) OTHER INFORMATION: /note="see seq id 1"

(xi) SEQUENCE DESCRIPTION: SEQ ID NO:7:

Phe  Asp  Trp  Phe  Xaa
1                    5

(2) INFORMATION FOR SEQ ID NO:8:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1..2
    (D) OTHER INFORMATION: /note="Cyclo(Arg(NO2)--
        Asp)"

(ix) FEATURE:
    (A) NAME/KEY: Modified-site
    (B) LOCATION: 3
    (D) OTHER INFORMATION: /note="trp(CHO)"

(ix) FEATURE:
    (A) NAME/KEY: Modified-site
    (B) LOCATION: 5
    (D) OTHER INFORMATION: /note="see seq id 1"

(xi) SEQUENCE DESCRIPTION: SEQ ID NO:8:

Arg  Asp  Trp  Phe  Xaa
1                    5

(2) INFORMATION FOR SEQ ID NO:9:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1..2
    (D) OTHER INFORMATION: /note="Cyclo(Abo-Asp)
        seq id 1"

(ix) FEATURE:
    (A) NAME/KEY: Modified-site
    (B) LOCATION: 5
    (D) OTHER INFORMATION: /note="see seq id 1"

(xi) SEQUENCE DESCRIPTION: SEQ ID NO:9:

Xaa Asp Trp Phe Xaa
1             5

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="Cyclo(Abo-Asp)
            see seq id
            1"

( i x ) FEATURE:
        ( A ) NAME/KEY: Modified-site
        ( B ) LOCATION: 3
        ( D ) OTHER INFORMATION: /note="trp(COOtBu)"

( i x ) FEATURE:
        ( A ) NAME/KEY: Modified-site
        ( B ) LOCATION: 5
        ( D ) OTHER INFORMATION: /note="seq id 1"

( x i ) SEQUENCE DESCRIPTION: SEQ ID NO:10:

Xaa Asp Trp Phe Xaa
1             5

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="Cyclo(abo-asp)
            see seq id
            1"

( i x ) FEATURE:
        ( A ) NAME/KEY: Modified-site
        ( B ) LOCATION: 5
        ( D ) OTHER INFORMATION: /note="see seq id 1"

( x i ) SEQUENCE DESCRIPTION: SEQ ID NO:11:

Xaa Asp Trp Phe Xaa
1             5

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="Cyclo(hyp-asp)
            hyp=4Hyp"

( i x ) FEATURE:
        ( A ) NAME/KEY: Modified-site
        ( B ) LOCATION: 3

( D ) OTHER INFORMATION: /note="trp(CHO)"

( i x ) FEATURE:
    ( A ) NAME/KEY: Modified-site
    ( B ) LOCATION: 5
    ( D ) OTHER INFORMATION: /note="see seq id 1"

( x i ) SEQUENCE DESCRIPTION: SEQ ID NO:12:

Xaa Asp Trp Phe Xaa
1                 5

( 2 ) INFORMATION FOR SEQ ID NO:13:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="Cyclo(Hyp-Asp)
            see seq id
            12"

( i x ) FEATURE:
        ( A ) NAME/KEY: Modified-site
        ( B ) LOCATION: 3
        ( D ) OTHER INFORMATION: /note="trp(CHO)"

( i x ) FEATURE:
        ( A ) NAME/KEY: Modified-site
        ( B ) LOCATION: 5
        ( D ) OTHER INFORMATION: /note="see seq id 1"

( x i ) SEQUENCE DESCRIPTION: SEQ ID NO:13:

Xaa Asp Trp Phe Xaa
1                 5

( 2 ) INFORMATION FOR SEQ ID NO:14:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="Cyclo(MePhe-Asp)
            see seq id
            7"

( i x ) FEATURE:
        ( A ) NAME/KEY: Modified-site
        ( B ) LOCATION: 4
        ( D ) OTHER INFORMATION: /note="N(CH3)CH2C6H5"

( x i ) SEQUENCE DESCRIPTION: SEQ ID NO:14:

Phe Asp Phe Xaa
1

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:

(A) NAME/KEY: Modified-site
(B) LOCATION: 1..2
(D) OTHER INFORMATION: /note="Cyclo(Tic-asp)
see seq id
3"

(ix) FEATURE:
(A) NAME/KEY: Modified-site
(B) LOCATION: 4
(D) OTHER INFORMATION: /note="see seq id 14"

(xi) SEQUENCE DESCRIPTION: SEQ ID NO:15:

Xaa Asp Phe Xaa
1

(2) INFORMATION FOR SEQ ID NO:16:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1..2
(D) OTHER INFORMATION: /note="Cyclo(Tic-Asp) see
seq id
3"

(ix) FEATURE:
(A) NAME/KEY: Modified-site
(B) LOCATION: 4
(D) OTHER INFORMATION: /note="see seq id 14"

(xi) SEQUENCE DESCRIPTION: SEQ ID NO:16:

Xaa Asp Phe Xaa
1

(2) INFORMATION FOR SEQ ID NO:17:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1..2
(D) OTHER INFORMATION: /note="Cyclo(Abo-Asp) see
seq id
1"

(ix) FEATURE:
(A) NAME/KEY: Modified-site
(B) LOCATION: 4
(D) OTHER INFORMATION: /note="see seq id 14"

(xi) SEQUENCE DESCRIPTION: SEQ ID NO:17:

Xaa Asp Phe Xaa
1

(2) INFORMATION FOR SEQ ID NO:18:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(A) NAME/KEY: Modified-site (B) LOCATION: 1..2
(D) OTHER INFORMATION: /note="Cyclo(Dht-asp)
Dht=6,7- dihydroxy-1,2,3,4-tetrahydroiso-
quinoline"

(ix) FEATURE:
(A) NAME/KEY: Modified-site
(B) LOCATION: 4
(D) OTHER INFORMATION: /note="see seq id 14"

(xi) SEQUENCE DESCRIPTION: SEQ ID NO:18:

Xaa Asp Phe Xaa
1

(2) INFORMATION FOR SEQ ID NO:19:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1..2
(D) OTHER INFORMATION: /note="Cyclo(Spi-asp)"

(ix) FEATURE:
(A) NAME/KEY: Modified-site
(B) LOCATION: 4
(D) OTHER INFORMATION: /note="see seq id 1"

(xi) SEQUENCE DESCRIPTION: SEQ ID NO:19:

Xaa Asp Phe Xaa
1

(2) INFORMATION FOR SEQ ID NO:20:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1..2
(D) OTHER INFORMATION: /note="Cyclo(Tic-asp)"

(ix) FEATURE:
(A) NAME/KEY: Modified-site
(B) LOCATION: 3
(D) OTHER INFORMATION: /note="Tic"

(ix) FEATURE:
(A) NAME/KEY: Modified-site
(B) LOCATION: 4
(D) OTHER INFORMATION: /note="see seq id 1"

(xi) SEQUENCE DESCRIPTION: SEQ ID NO:20:

Xaa Asp Xaa Xaa
1

(2) INFORMATION FOR SEQ ID NO:21:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(A) NAME/KEY: Modified-site ( B ) LOCATION: 1..2
                    ( D ) OTHER INFORMATION: /note="Cyclo(abo-asp) see
                            seq id
                            1"

( i x ) FEATURE:
                    ( A ) NAME/KEY: Modified-site
                    ( B ) LOCATION: 4
                    ( D ) OTHER INFORMATION: /note="see seq id 1"

( x i ) SEQUENCE DESCRIPTION: SEQ ID NO:21:

Xaa  Asp  Phe  Xaa
    1

( 2 ) INFORMATION FOR SEQ ID NO:22:

( i ) SEQUENCE CHARACTERISTICS:
                ( A ) LENGTH: 4 amino acids
                ( B ) TYPE: amino acid
                ( D ) TOPOLOGY: linear ( i i ) MOLECULE TYPE: peptide ( i x ) FEATURE:
                ( A ) NAME/KEY: Modified-site
                ( B ) LOCATION: 1..2
                ( D ) OTHER INFORMATION: /note="Cyclo(tic-asp) see
                        seq id3"

( i x ) FEATURE:
                ( A ) NAME/KEY: Modified-site
                ( B ) LOCATION: 4
                ( D ) OTHER INFORMATION: /note="see seq id 14"

( x i ) SEQUENCE DESCRIPTION: SEQ ID NO:22:

Xaa  Asp  Phe  Xaa
    1

( 2 ) INFORMATION FOR SEQ ID NO:23:

( i ) SEQUENCE CHARACTERISTICS:
                ( A ) LENGTH: 5 amino acids
                ( B ) TYPE: amino acid
                ( D ) TOPOLOGY: linear ( i i ) MOLECULE TYPE: peptide ( i x ) FEATURE:
                ( A ) NAME/KEY: Modified-site
                ( B ) LOCATION: 1..2
                ( D ) OTHER INFORMATION: /note="Cyclo(Tic-asp)"

( i x ) FEATURE:
                ( A ) NAME/KEY: Modified-site
                ( B ) LOCATION: 3
(CH2S)"         ( D ) OTHER INFORMATION: /note="

( i x ) FEATURE:
                ( A ) NAME/KEY: Modified-site
                ( B ) LOCATION: 5
                ( D ) OTHER INFORMATION: /note="see seq id 1"

( x i ) SEQUENCE DESCRIPTION: SEQ ID NO:23:

Xaa  Asp  Xaa  Phe  Xaa
    1                  5

( 2 ) INFORMATION FOR SEQ ID NO:24:

( i ) SEQUENCE CHARACTERISTICS:
                ( A ) LENGTH: 5 amino acids
                ( B ) TYPE: amino acid
                ( D ) TOPOLOGY: linear ( i i ) MOLECULE TYPE: peptide ( i x ) FEATURE:

(A) NAME/KEY: Modified-site
(B) LOCATION: 1..2
(D) OTHER INFORMATION: /note="Cyclo(Tic-asp)"

(ix) FEATURE:
(A) NAME/KEY: Modified-site
(B) LOCATION: 3
(D) OTHER INFORMATION: /note="(CH2S)"

(ix) FEATURE:
(A) NAME/KEY: Modified-site
(B) LOCATION: 5
(D) OTHER INFORMATION: /note="see seq id 1"

(xi) SEQUENCE DESCRIPTION: SEQ ID NO:24:

Xaa Asp Xaa Phe Xaa
1               5

(2) INFORMATION FOR SEQ ID NO:25:

(i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1..2
(D) OTHER INFORMATION: /note="Cyclo(Abo-Asp)"

(ix) FEATURE:
(A) NAME/KEY: Modified-site
(B) LOCATION: 3
(D) OTHER INFORMATION: /note="trp(CHO)"

(ix) FEATURE:
(A) NAME/KEY: Modified-site
(B) LOCATION: 5
(D) OTHER INFORMATION: /note="see seq id 1"

(ix) FEATURE:
(A) NAME/KEY: Modified-site
(B) LOCATION: 4
(D) OTHER INFORMATION: /note="Tic"

(xi) SEQUENCE DESCRIPTION: SEQ ID NO:25:

Xaa Asp Trp Xaa Xaa
1               5

(2) INFORMATION FOR SEQ ID NO:26:

(i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1..2
(D) OTHER INFORMATION: /note="Cyclo(Abo-Asp)"

(ix) FEATURE:
(A) NAME/KEY: Modified-site
(B) LOCATION: 3
(D) OTHER INFORMATION: /note="trp(CHO)"

(ix) FEATURE:
(A) NAME/KEY: Modified-site
(B) LOCATION: 5
(D) OTHER INFORMATION: /note="see seq id 1"

(xi) SEQUENCE DESCRIPTION: SEQ ID NO:26:

Xaa Asp Trp Tyr Xaa (2) INFORMATION FOR SEQ ID NO:27:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..2
        (D) OTHER INFORMATION: /note="Cyclo(Abo-Asp)"

(ix) FEATURE:
        (A) NAME/KEY: Modified-site
        (B) LOCATION: 3
        (D) OTHER INFORMATION: /note="Pya (pyridinylalanine)"

(ix) FEATURE:
        (A) NAME/KEY: Modified-site
        (B) LOCATION: 4
        (D) OTHER INFORMATION: /note="see seq id 14"

(xi) SEQUENCE DESCRIPTION: SEQ ID NO:27:

Xaa Asp Xaa Xaa
1

(2) INFORMATION FOR SEQ ID NO:28:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..2
        (D) OTHER INFORMATION: /note="Cyclo(Abo-Asp)"

(ix) FEATURE:
        (A) NAME/KEY: Modified-site
        (B) LOCATION: 4
        (D) OTHER INFORMATION: /note="Pya (pyridinylalanine"

(ix) FEATURE:
        (A) NAME/KEY: Modified-site
        (B) LOCATION: 5
        (D) OTHER INFORMATION: /note="see seq id 1"

(ix) FEATURE:
        (A) NAME/KEY: Modified-site
        (B) LOCATION: 3
        (D) OTHER INFORMATION: /note="trp"

(xi) SEQUENCE DESCRIPTION: SEQ ID NO:28:

Xaa Asp Trp Xaa Xaa
1                  5

(2) INFORMATION FOR SEQ ID NO:29:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..2

(D) OTHER INFORMATION: /note="CycloAbo-Asp)"

(ix) FEATURE:
    (A) NAME/KEY: Modified-site
    (B) LOCATION: 3
    (D) OTHER INFORMATION: /note="trp(CH3)"

(ix) FEATURE:
    (A) NAME/KEY: Modified-site
    (B) LOCATION: 5
    (D) OTHER INFORMATION: /note="see seq id 1"

(xi) SEQUENCE DESCRIPTION: SEQ ID NO:29:

Xaa Asp Trp Phe Xaa
1               5

(2) INFORMATION FOR SEQ ID NO:30:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..2
        (D) OTHER INFORMATION: /note="Cyclo(Abo-Asp)"

(ix) FEATURE:
        (A) NAME/KEY: Modified-site
        (B) LOCATION: 3
        (D) OTHER INFORMATION: /note="nal (beta-naph-
            thylalanine)"

(ix) FEATURE:
        (A) NAME/KEY: Modified-site
        (B) LOCATION: 5
        (D) OTHER INFORMATION: /note="see seq id 1"

(xi) SEQUENCE DESCRIPTION: SEQ ID NO:30:

Xaa Asp Xaa Phe Xaa
1               5

(2) INFORMATION FOR SEQ ID NO:31:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="(indol-3-yl)
            carbonyl"

(ix) FEATURE:
        (A) NAME/KEY: Modified-site
        (B) LOCATION: 2
        (D) OTHER INFORMATION: /note="Abo"

(ix) FEATURE:
        (A) NAME/KEY: Modified-site
        (B) LOCATION: 4
        (D) OTHER INFORMATION: /label=c
            / note="see seq id 14"

(xi) SEQUENCE DESCRIPTION: SEQ ID NO:31:

Xaa Xaa Phe Xaa
1

(2) INFORMATION FOR SEQ ID NO:32:

( i ) SEQUENCE CHARACTERISTICS:
  ( A ) LENGTH: 5 amino acids
  ( B ) TYPE: amino acid
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note="Boc (tert-butoxy-carbonyl)"

( i x ) FEATURE:
  ( A ) NAME/KEY: Modified-site
  ( B ) LOCATION: 2
  ( D ) OTHER INFORMATION: /note="Abo"

( i x ) FEATURE:
  ( A ) NAME/KEY: Modified-site
  ( B ) LOCATION: 3
  ( D ) OTHER INFORMATION: /note="nal"

( i x ) FEATURE:
  ( A ) NAME/KEY: Modified-site
  ( B ) LOCATION: 5
  ( D ) OTHER INFORMATION: /note="see seq id 1"

( x i ) SEQUENCE DESCRIPTION: SEQ ID NO:32:

Xaa Xaa Xaa Phe Xaa
1               5

( 2 ) INFORMATION FOR SEQ ID NO:33:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Boc"

( i x ) FEATURE:
    ( A ) NAME/KEY: Modified-site
    ( B ) LOCATION: 2
    ( D ) OTHER INFORMATION: /note="abo"

( i x ) FEATURE:
    ( A ) NAME/KEY: Modified-site
    ( B ) LOCATION: 3
    ( D ) OTHER INFORMATION: /note="nal"

( i x ) FEATURE:
    ( A ) NAME/KEY: Modified-site
    ( B ) LOCATION: 5
    ( D ) OTHER INFORMATION: /note="see seq id 1"

( x i ) SEQUENCE DESCRIPTION: SEQ ID NO:33:

Xaa Xaa Xaa Phe Xaa
1               5

( 2 ) INFORMATION FOR SEQ ID NO:34:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1

( D ) OTHER INFORMATION: /note="H"

( i x ) FEATURE:
    ( A ) NAME/KEY: Modified-site
    ( B ) LOCATION: 2
    ( D ) OTHER INFORMATION: /note="trp"

( i x ) FEATURE:
    ( A ) NAME/KEY: Modified-site
    ( B ) LOCATION: 3
    ( D ) OTHER INFORMATION: /note="(CH2S)"

( i x ) FEATURE:
    ( A ) NAME/KEY: Modified-site
    ( B ) LOCATION: 5
    ( D ) OTHER INFORMATION: /note="Abo"

( i x ) FEATURE:
    ( A ) NAME/KEY: Modified-site
    ( B ) LOCATION: 7
    ( D ) OTHER INFORMATION: /note="NH2"

( x i ) SEQUENCE DESCRIPTION: SEQ ID NO:34:

Xaa Trp Xaa Phe Xaa Phe Xaa
1               5

( 2 ) INFORMATION FOR SEQ ID NO:35:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: mRNA ( i x ) FEATURE:
        ( A ) NAME/KEY: Modified-site
        ( B ) LOCATION: 1
        ( D ) OTHER INFORMATION: /note="H"

( i x ) FEATURE:
        ( A ) NAME/KEY: Modified-site
        ( B ) LOCATION: 2
        ( D ) OTHER INFORMATION: /note="trp"

( i x ) FEATURE:
        ( A ) NAME/KEY: Modified-site
        ( B ) LOCATION: 4
        ( D ) OTHER INFORMATION: /note="Abo"

( i x ) FEATURE:
        ( A ) NAME/KEY: Modified-site
        ( B ) LOCATION: 6
        ( D ) OTHER INFORMATION: /note="NH2, CF3CO2H"

( x i ) SEQUENCE DESCRIPTION: SEQ ID NO:35:

Xaa Xaa Xaa Phe Xaa Xaa
1               5

( 2 ) INFORMATION FOR SEQ ID NO:36:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Z"

( i x ) FEATURE:
        ( A ) NAME/KEY: Modified-site
        ( B ) LOCATION: 3
        ( D ) OTHER INFORMATION: /note="abo"

( i x ) FEATURE:
    ( A ) NAME/KEY: Modified-site
    ( B ) LOCATION: 4
    ( D ) OTHER INFORMATION: /note="trp"

( i x ) FEATURE:
    ( A ) NAME/KEY: Modified-site
    ( B ) LOCATION: 5
    ( D ) OTHER INFORMATION: /note="NH2"

( x i ) SEQUENCE DESCRIPTION: SEQ ID NO:36:

Xaa Phe Xaa Trp Xaa
1                 5

( 2 ) INFORMATION FOR SEQ ID NO:37:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: mRNA ( i x ) FEATURE:
        ( A ) NAME/KEY: Modified-site
        ( B ) LOCATION: 1
        ( D ) OTHER INFORMATION: /note="Benzhydryl
            carbonyl"

( i x ) FEATURE:
        ( A ) NAME/KEY: Modified-site
        ( B ) LOCATION: 2
        ( D ) OTHER INFORMATION: /note="Abo"

( i x ) FEATURE:
        ( A ) NAME/KEY: Modified-site
        ( B ) LOCATION: 5
        ( D ) OTHER INFORMATION: /note="NH2"

( x i ) SEQUENCE DESCRIPTION: SEQ ID NO:37:

Xaa Xaa Leu Trp Xaa
1                 5

( 2 ) INFORMATION FOR SEQ ID NO:38:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="Cyclo(Abo-Asp)"

( i x ) FEATURE:
        ( A ) NAME/KEY: Modified-site
        ( B ) LOCATION: 3
        ( D ) OTHER INFORMATION: /note="trp(CO(CH2)6NH2,-
            HCl)"

( i x ) FEATURE:
        ( A ) NAME/KEY: Modified-site
        ( B ) LOCATION: 5
        ( D ) OTHER INFORMATION: /note="see seq id 1"

( x i ) SEQUENCE DESCRIPTION: SEQ ID NO:38:

Xaa Asp Trp Phe Xaa
1                 5

( 2 ) INFORMATION FOR SEQ ID NO:39:

( i ) SEQUENCE CHARACTERISTICS:
        ( A ) LENGTH: 5 amino acids ( B ) TYPE: amino acid
( D ) TOPOLOGY: linear ( i i ) MOLECULE TYPE: peptide ( i x ) FEATURE:
    ( A ) NAME/KEY: Modified-site
    ( B ) LOCATION: 1..2
    ( D ) OTHER INFORMATION: /note="Cyclo(Abo-Asp)"

( i x ) FEATURE:
    ( A ) NAME/KEY: Modified-site
    ( B ) LOCATION: 3
    ( D ) OTHER INFORMATION: /note="trp(CO(CH2)2COOH)"

( i x ) FEATURE:
    ( A ) NAME/KEY: Modified-site
    ( B ) LOCATION: 5
    ( D ) OTHER INFORMATION: /note="see seq id 1"

( x i ) SEQUENCE DESCRIPTION: SEQ ID NO:39:

Xaa Asp Trp Phe Xaa
1               5

( 2 ) INFORMATION FOR SEQ ID NO:40:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="Cyclo(Abo-Asp)"

( i x ) FEATURE:
        ( A ) NAME/KEY: Modified-site
        ( B ) LOCATION: 3
        ( D ) OTHER INFORMATION: /note="trp(COO(CH2)6NH2,-HCl)"

( i x ) FEATURE:
        ( A ) NAME/KEY: Modified-site
        ( B ) LOCATION: 5
        ( D ) OTHER INFORMATION: /note="see seq id 1"

( x i ) SEQUENCE DESCRIPTION: SEQ ID NO:40:

Xaa Asp Trp Phe Xaa
1               5

( 2 ) INFORMATION FOR SEQ ID NO:41:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="Cyclo(Abo-Asp)"

( i x ) FEATURE:
        ( A ) NAME/KEY: Modified-site
        ( B ) LOCATION: 3
        ( D ) OTHER INFORMATION: /note="trp(COO(CH2)6NH2,-HCl)"

( i x ) FEATURE:
        ( A ) NAME/KEY: Modified-site
        ( B ) LOCATION: 5
        ( D ) OTHER INFORMATION: /note="see seq id 1"

( x i ) SEQUENCE DESCRIPTION: SEQ ID NO:41:

Xaa Asp Trp Phe Xaa
1               5

( 2 ) INFORMATION FOR SEQ ID NO:42:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1..2
      ( D ) OTHER INFORMATION: /note="Cyclo(Abo-Asp)"

( i x ) FEATURE:
      ( A ) NAME/KEY: Modified-site
      ( B ) LOCATION: 3
      ( D ) OTHER INFORMATION: /note="trp(COOCH2C6H5)"

( i x ) FEATURE:
      ( A ) NAME/KEY: Modified-site
      ( B ) LOCATION: 5
      ( D ) OTHER INFORMATION: /note="see seq id 1"

( x i ) SEQUENCE DESCRIPTION: SEQ ID NO:42:

Xaa Asp Trp Phe Xaa
1               5

( 2 ) INFORMATION FOR SEQ ID NO:43:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1..2
      ( D ) OTHER INFORMATION: /note="Cyclo(Abo-Asp)"

( i x ) FEATURE:
      ( A ) NAME/KEY: Modified-site
      ( B ) LOCATION: 3
      ( D ) OTHER INFORMATION: /note="trp(COOCH2C6H5)"

( i x ) FEATURE:
      ( A ) NAME/KEY: Modified-site
      ( B ) LOCATION: 5
      ( D ) OTHER INFORMATION: /note="see seq id 1"

( x i ) SEQUENCE DESCRIPTION: SEQ ID NO:43:

Xaa Asp Trp Phe Xaa
1               5

( 2 ) INFORMATION FOR SEQ ID NO:44:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1..2
      ( D ) OTHER INFORMATION: /note="Cyclo(Abo-Asp)"

( i x ) FEATURE:
      ( A ) NAME/KEY: Modified-site

-continued

```
        ( B ) LOCATION: 3
        ( D ) OTHER INFORMATION: /note="trp(COOCH3)"

( i x ) FEATURE:
        ( A ) NAME/KEY: Modified-site
        ( B ) LOCATION: 5
        ( D ) OTHER INFORMATION: /note="see seq id 1"

( x i ) SEQUENCE DESCRIPTION: SEQ ID NO:44:

Xaa Asp Trp Phe Xaa
  1               5
```

( 2 ) INFORMATION FOR SEQ ID NO:45:

```
    ( i ) SEQUENCE CHARACTERISTICS:
            ( A ) LENGTH: 5 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 1..2
            ( D ) OTHER INFORMATION: /note="Cyclo(Abo-Asp)"

( i x ) FEATURE:
            ( A ) NAME/KEY: Modified-site
            ( B ) LOCATION: 3
            ( D ) OTHER INFORMATION: /note="trp(COCH3)"

( i x ) FEATURE:
            ( A ) NAME/KEY: Modified-site
            ( B ) LOCATION: 5
            ( D ) OTHER INFORMATION: /note="see seq id 1"

( x i ) SEQUENCE DESCRIPTION: SEQ ID NO:45:

Xaa Asp Trp Phe Xaa
  1               5
```

( 2 ) INFORMATION FOR SEQ ID NO:46:

```
    ( i ) SEQUENCE CHARACTERISTICS:
            ( A ) LENGTH: 5 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 1..2
            ( D ) OTHER INFORMATION: /note="Cyclo(Abo-Asp)"

( i x ) FEATURE:
            ( A ) NAME/KEY: Modified-site
            ( B ) LOCATION: 3
            ( D ) OTHER INFORMATION: /note="trp(Fmoc)
                    Fmoc=9- fluorenylmethoxycarbonyl"

( i x ) FEATURE:
            ( A ) NAME/KEY: Modified-site
            ( B ) LOCATION: 5
            ( D ) OTHER INFORMATION: /note="see seq id 1"

( x i ) SEQUENCE DESCRIPTION: SEQ ID NO:46:

Xaa Asp Trp Phe Xaa
  1               5
```

PEPTIDES AND PSEUDOPEPTIDES DERIVED FROM TACHYKININ

The present invention relates to novel peptides and pseudopeptides derived from tachykinins, a process for their preparation and the pharmaceutical compositions containing these.

The tachykinins form a family of peptides producing rapid contractions of the smooth muscular fibers, as opposed to the slow contractions caused by the bradykinins. Substance P, neurokinin A and neurokinin B make up the principal endogenous tachykinins corresponding respectively to the receptors $NK_1$, $NK_2$ and $NK_3$.

Numerous antagonist peptides of tachykinin have been described in the literature. This is the case, for example, for the compounds described in the Patents EP-A-333174 and EP-A-394989.

The subject of the present invention is synthetic peptides which, apart from the fact that they are novel, have been shown to be particularly advantageous by virtue of the strength of their pharmacological properties. They not only possess powerful antagonistic properties with respect to receptors for tachykinins but more particularly selective and intense properties with respect to $NK_1$ receptors, that is to say of substance P. These properties make them useful more particularly in the treatment of pain, inflammation, gastrointestinal disorders, asthma, allergies and diseases of the central nervous system.

The invention more particularly relates to novel peptide compounds corresponding to the general formula (I):

in which:

$R_1$ and $R_2$, which are identical or different, represent hydrogen, a linear or branched ($C_1$-$C_6$) alkyl, ($C_3$-$C_7$) cycloalkyl or benzyl, B represents a residue of an aromatic amino acid, A represents either a peptide residue of formula:

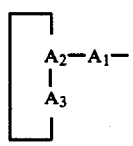

in which:

$A_1$ represents a bond, a residue 2-azabicyclo[2.2.2]octane-3-carbonyl (Abo), leucine (Leu), β-naphthylalanine (Nal), tryptophan (Trp) or tryptophan protected by a radical Q (Trp (Q)), Q representing the radical

—X—(CH$_2$)n—R' in which

X represents a bond, —CO— or —COO—, n is an integer from 0 to 10,

R' is hydrogen, linear or branched ($C_1$-$C_{10}$) alkyl, benzyl, 9-fluorenylmethyl, —NH$_2$, —COOH or —COOR'' (R''=linear or branched ($C_1$-$C_6$) alkyl), $A_2$ represents an aspartic acid residue (Asp) or glutamic acid residue (Glu), $A_3$ represents a residue 1,2,3,4-tetrahydroisoquinoline-3-carbonyl (Tic), 2-azabicyclo[2.2.2]octane-3-carbonyl (Abo), methylphenylalanine (MePhe), arginine (Arg), arginine protected by a nitro radical (Arg (NO$_2$)), 6,7-dihydroxy-1,2,3,4-tetrahydroisoquinoline (Dht), spinacine (Spi), 4-hydroxyproline (Hyp), β-naphthylalanine (Nal) or proline (Pro).

it being understood that the peptide bond (—CO—NH—) between $A_1$ and $A_2$ or between $A_2$ and B in the case where $A_1$ is a bond, can be replaced by a pseudopeptide bond chosen from amongst —CH$_2$—NH— and —CH$_2$—S—, or a peptide residue of formula:

P—A$_6$—A$_5$—A$_4$— in which:

$A_4$ represents a residue 2-azabicyclo[2.2.2]octane-3-carbonyl (Abo), leucine (Leu) or β-naphthylalanine (Nal).

$A_5$ represents a bond or a residue phenylalanine (Phe), β-naphthylalanine (Nal) or 2-azabicyclo[2.2.2]octane-3-carbonyl (Abo), $A_6$ represents a bond or a residue tryptophan (Trp), tryptophan protected by a formyl radical (Trp (CHO)), tryptophan protected by a methyl radical (Trp (CH$_3$)), or 2-azabicyclo[2.2.2]octane-3-carbonyl (Abo), P represents a hydrogen atom or a group protecting the amine function such as benzyloxycarbonyl (Z), tert-butoxycarbonyl (Boc), 3-indolylcarbonyl, benzhydrylcarbonyl or 9-fluorenylmethoxycarbonyl (Fmoc), it being understood that the peptide bond (—CO—NH—) between $A_5$ and $A_6$, in the case where $A_5$ and $A_6$ are not bonds, can be replaced by a pseudopeptide bond chosen from amongst —CH$_2$—NH— and —CH$_2$—S—, their enantiomers, diastereoisomers and epimers as well as their pharmaceutically acceptable acid or base addition salts, it being understood that each amino acid of the peptide sequence is optically pure and that the α carbon of each amino acid can be of D or L configuration.

Aromatic amino acid residue is more particularly understood to mean a residue phenylalanine (Phe), tyrosine (Tyr), 1,2,3,4-tetrahydroisoquinoline-3-carbonyl (Tic), tryptophan (Trp), tryptophan protected by a formyl radical (Trp (CHO)) or pyridinylalanine (Pya).

Among the pharmaceutically acceptable acids, those which can be cited in a non-restrictive manner are hydrochloric, hydrobromic, sulfuric, phosphonic, acetic, trifluoroacetic, lactic, pyruvic, malonic, succinic, glutaric, fumaric, tartaric, maleic, citric, ascorbic, oxalic, methanesulfonic and camphoric acids, etc. . . .

Among the pharmaceutically acceptable bases, those which can be cited in a non-restrictive manner are sodium hydroxide, potassium hydroxide, triethylamine and tert-butylamine, etc. . . .

The invention also extends to the process for the preparation of the compounds of formula (I) which can be obtained by different methods, such as sequential synthesis on a solid phase, enzymatic synthesis, genetic synthesis by cloning and expression of the genes in transformed bacteria or by various combinations of these techniques.

The peptides of the present invention are generally obtained by coupling in solution of selectively protected peptide fragments, which can be prepared either on a solid phase or in solution.

The general methods for the synthesis of peptides on a solid phase have been described by B. W. ERICKSON and R. B. MERRIFIELD ("The Proteins", Solid-Phase Peptide Synthesis, 3rd edition, 257–527, 1976).

More specifically, the process for the preparation of the compounds of the invention follows the method of synthesis and of coupling of the fragments in solution, properly adapted to the size and to the modifications of the compounds.

This process comprises reacting an optically pure amide of formula (II):

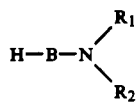
(II)

in which B, $R_1$ and $R_2$ have the same meaning as in formula (I) with a second optically pure amino acid, in which the N-terminal amine function is protected, of formula (III) or (IV), according to the compound of formula (I) which it is desired to obtain:

$$P_1-A_1-OH \quad (III)$$

$$P_1-A_4-OH \quad (IV)$$

in which:
$P_1$ represents a protective group chosen from amongst benzyloxycarbonyl (Z), tert-butyloxycarbonyl (Boc) and 9-fluorenylmethoxycarbonyl (Fmoc), and
$A_1$ and $A_2$ have the same meaning as in formula (I),
in the presence of a conventional coupling reagent of peptide synthesis chosen from amongst the pair dicyclohexylcarbodiimide (DCC)-hydroxybenzotriazole (HOBT), benzotriazole-1-oxytris(dimethylamino) phosphonium hexafluorophosphate (BOP) or else diphenylphosphoryl azide (DPPA), to lead respectively, after selective deprotection of the N-terminal amine function, to the compounds of formulae (V) and (VI), according to the derivative of formula (I) which it is desired to obtain:

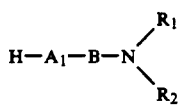
(V)

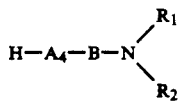
(VI)

in which $A_1$, $A_4$, B, $R_1$ and $R_2$ have the same meanings as in formula (I), the compound of formula (V) which is reacted with a compound of formula (VII):

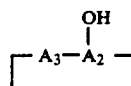
(VII)

in which $A_2$ and $A_3$ have the same meaning as in formula (I) (derivative of formula (VII) itself obtained by conventional peptide coupling of the protected optically pure amino acids $A_3$-OH and $A_2$-OH, cyclization to the corresponding diketopiperazine in basic medium, deprotection and purification), in the presence of a conventional coupling reagent of peptide synthesis described above, to lead to a compound of formula (I/a), in the particular case of the compounds of formula (I),

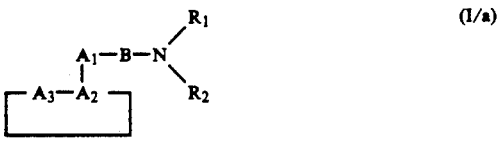
(I/a)

in which $A_1$, $A_2$, $A_3$, B, $R_1$ and $R_2$ have the same meaning as in formula (I), the radical $A_1$, when it represents a tryptophan residue which can be optionally protected by an appropriate reagent, containing the radical Q, for example Q-Cl, in the presence of reagents and of solvents suitable in this case, such as sodium hydroxide and tetrabutylammonium hydrogenosulfate in methylene chloride, the compound of formula (VI) which is reacted with a compound of formula (VIII):

$$P_1-A_6-A_5-OH \quad (VIII)$$

in which $P_1$ has the same meaning as above, and $A_5$ and $A_6$ have the same meaning as in formula (I), (derivative of formula (VIII), itself obtained by conventional peptide coupling of the protected amino acids $A_5$-OH and $A_6$-OH), in the presence of a conventional coupling reagent of peptide synthesis described above, to lead, after customary treatment, to a compound of formula (I/b), in the particular case of the compounds of formula (I)

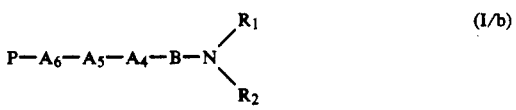
(I/b)

in which $A_4$, $A_5$, $A_6$, B, $R_1$, $R_2$ and P have the same meaning as in formula (I), the radical $A_4$, when it represents a tryptophan residue, can be optionally protected by an appropriate reagent, containing the radical Q, for example Q-Cl, in the presence of reagents and of solvents suitable in this case, such as sodium hydroxide and tetrabutylammonium sulfate in methylene chloride, the compounds of formula (I/a) or (I/b): which are purified by a conventional purification technique, which are converted, if necessary, into their pharmaceutically acceptable acid or base addition salts, which, when they contain a pseudopeptide bond —CH$_2$—NH— or —CH$_2$—S— are prepared according to the process described above, the introduction of the —CH$_2$—NH— bond being carried out by preparing the aldehyde $P_1$—NH—CHR—CHO in solution ($P_1$=protective group chosen from amongst Boc, Fmoc and Z) according to the technique described by FEHRENTZ and CASTRO (Synthesis, 676–678, 1983) and by condensing it with the growing peptide chain either on a solid phase, according to the technique described by SASAKI and COY (Peptides, 8, 119–121, 1988) or in solution, the introduction of the —CH₂—S— bond being carried out by condensing the thiol of formula P₁—NH—CHR—CH₂SH, prepared starting from the corresponding alcohol, with the C-terminal deaminopeptide bromide.

The compounds of the invention have very advantageous pharmacological properties. They are ligands specific for tackykinine receptors which have antagonistic properties with respect to NK₁, NK₂ and NK₃ receptors. These antagonistic properties are particularly intense with respect to NK₁ receptors. The NK₁ and NK₃ receptors are involved in the regulation of the transmission of pain and the increase in vascular permeability. In addition, the stimulation of NK₁ receptors induces hypersalivation, that of NK₂ receptors causes tachycardia, hypotension and bronchoconstriction, and finally that of NK₃ receptors is followed by bradycardia, hypotension and peripheral vasodilation (D. REGOLI et al., TIPS, 9, 290–295, 1988).

The present invention likewise relates to pharmaceutical compositions containing, as active principle, at least one compound of general formula (I) or one of its pharmaceutically acceptable acid addition salts, on its own or in combination with one or more inert, non-toxic excipients or vehicles.

Among the pharmaceutical compositions according to the invention, it is possible to cite more particularly those which are suitable for oral, parenteral or nasal administration, simple or coated tablets, sublingual tablets, sachets, packets, gelatin capsules, sublingual preparations, lozenges, suppositories, creams, ointments, dermal gels and aerosols.

The dosage varies according to the age and the weight of the patient, the nature and the severity of the ailment as well as the route of administration.

The latter can be oral, nasal, rectal or parenteral. Generally, the dosage ranges from between 0.2 and 100 mg for a treatment of one or more administrations per 24 hours.

The following examples illustrate the invention without limiting it in any manner.

The amino acids whose abbreviations commence with a capital letter are of L configuration.

The amino acids whose abbreviations commence with a small letter are of D configuration.

The letter ψ indicates the presence of a pseudopeptide bond whose nature is indicated in brackets.

The following preparations do not enable the compounds of the invention to be obtained but lead to intermediates which are useful in the preparation of the compounds of the invention.

PREPARATION A

H—Phe—N(CH₃)(CH₂C₆H₅, CF₃CO₂H)

60 mmol of Boc-Phe-OH and 60 mmol of methylbenzylamine are dissolved in 150 ml of dimethylformamide. 60 mmol of hydroxybenzotriazole (HOBT) in 100 ml of dimethylformamide and then 80 mmol of dicyclohexylcarbodiimide (DCC) dissolved in 40 ml of dimethylformamide are added to the above mixture. Stirring is continued for 16 hours at room temperature.

After filtration of the dicyclohexylurea formed and evaporation of the solvent, the residue is taken up with ethyl acetate and the organic phase is washed with a 5% sodium hydrogencarbonate solution and then with a potassium sulfate solution and finally with a saturated sodium chloride solution.

After evaporation of the solvent, the crude residue is purified by chromatography on a silica column. The terminal amine function of the phenylalanine is deprotected by treatment of the compound obtained for 20 minutes in trifluoroacetic acid or in gaseous chlorhydric acid in ethylacetate, the expected product is thus obtained in the form of salt. Yield: 92%

PREPARATION B

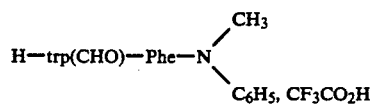

50 mmol of the compound obtained in preparation A are dissolved in 100 ml of dimethylformamide in the presence of 50 mmol of triethylamine. A solution containing 50 mmol of Boc-trp (CHO)—OH and 50 mmol of HOBT in 70 ml of dimethylformamide is added to the above mixture, followed by the addition of a solution containing 70 mmol of DCC in 30 ml of dimethylformamide. The whole is kept stirred for 16 hours at room temperature. The expected product in the form of trifluoroacetate is isolated, purified and deprotected proceeding as in preparation A. Yield: 78%

EXAMPLE 1

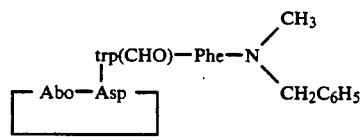

Step A: Fmoc-Asp (OtBu)-Abo-OMe 35 mmol of H-Abo-OMe.HCL are dissolved in 70 ml of dimethylformamide in the presence of 35 mmol of triethylamine. A solution containing 35 mmol of Fmoc-Asp (OtBu)-OH and 35 mmol of HOBT is then added to the above mixture, followed by the addition of a solution containing 42 mmol of DCC in 20 ml of dimethylformamide. The whole is kept stirred for 14 hours at room temperature. The expected product is isolated proceeding as in preparation A and purified by chromatography on a silica column using as solvent for elution a mixture of ethyl acetate/pentane: 1:1. Yield: 96%

Step B

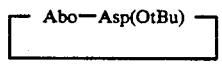

12 mmol of the compound obtained in the above step are dissolved in 60 ml of a dimethylformamide/piperidine mixture (80:20). The whole is kept stirred for 15 minutes at room temperature.

After cooling and evaporation of the solvent, the expected product is obtained and purified on a silica column using ethyl acetate as solvent for elution. Yield: 69%

Step C

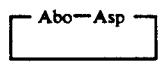

9 mmol of the compound obtained in the above stage are dissolved in 80 ml of a dichloromethane/acetic acid mixture (50:50) and the whole is stirred for 1 hour at room temperature.

After evaporation of the solvents, the residue is taken up with ethyl ether. The expected product precipitates, and is isolated by filtration, then washed and dried.

Yield: 69%

Step D

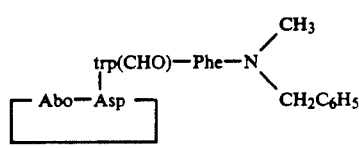

1.7 mmol of the compound obtained in preparation B are dissolved in 15 ml of dimethylformamide in the presence of 1.7 mmol of triethylamine. A solution containing 1.7 mmol of the compound obtained in Step C and 1.7 mmol of HOBT in 12 ml of dimethylformamide is added to the above mixture, followed by the addition of a solution containing 1.8 mmol of DCC in 1 ml of dimethylformamide. The whole is kept stirred for 14 hours at room temperature. The expected product is isolated proceeding as in preparation A and purified by chromatography on $C_{18}$ silica using as solvent for elution an acetonitrile/water/trifluoroacetic acid mixture (40:60:0.2).

Yield: 64%

Mass spectrum (FAB) MH+:m/e=717 (molecular weight: 716.8)

The analysis of the product obtained is carried out after decomposition of the latter into amino acids by acid hydrolysis and a quantitative determination of the amino acids obtained by liquid chromatography:

|   | Abo | Asp | Phe + Trp |
|---|-----|-----|-----------|
| % calculated | 1 | 1 | 2 |
| % found | 1.09 | 1.09 | 1.82 |

The following examples were obtained using the same synthesis process as that described in Example 1.

EXAMPLE 2

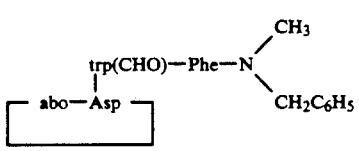

Mass spectrum (Fab):MH+:m/e=717 (molecular weight: 716.8)

EXAMPLE 3

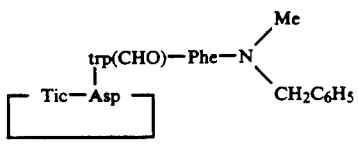

Mass spectrum (FAB):MH+:m/e=739 (molecular weight: 738.8)

EXAMPLE 4

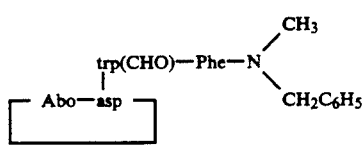

Mass spectrum (FAB):MH+:m/e=717 (molecular weight: 716.8)

EXAMPLE 5

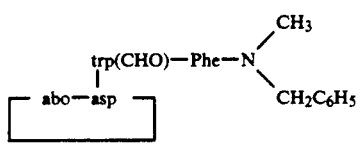

Mass spectrum (FAB):MH+:m/e=717 (molecular weight: 716.8)

EXAMPLE 6

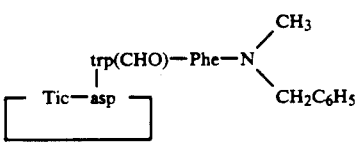

Mass spectrum (FAB):MH+:m/e=739 (molecular weight: 738.8)

EXAMPLE 7

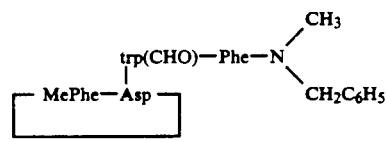

Mass spectrum (FAB):MH+:m/e=741 (molecular weight: 740.8)

EXAMPLE 8

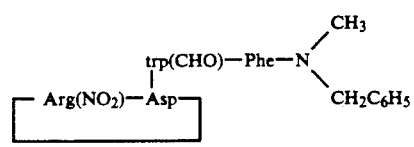

Mass spectrum (FAB):MH+:m/e=781 (molecular weight: 780.8)

EXAMPLE 9

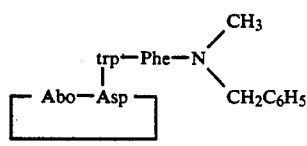

Mass spectrum (FAB):MH+:m/e=689 (molecular weight: 688.8)

EXAMPLE 10

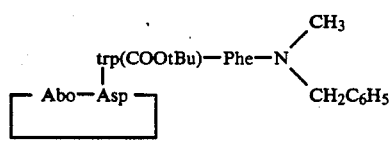

Compound obtained as described in example 9 tryptophane protection being carried out with (Boc)₂O in the presence of trimethylaminopyridine.

Mass spectrum (FAB):MH+:m/e=789 (molecular weight: 788)

EXAMPLE 11

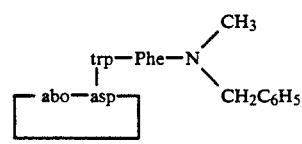

Mass spectrum (FAB):MH+:m/e=689 (molecular weight: 688.8)

EXAMPLE 12

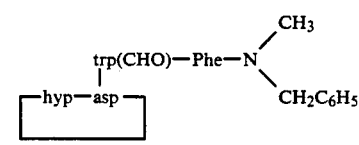

Mass spectrum (FAB):MH+:m/e=693 (molecular weight: 692.8)

EXAMPLE 13

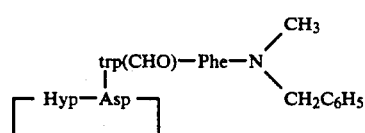

Mass spectrum (FAB):MH+:m/e=693 (molecular weight: 692.8)

In the following examples, the procedure is as in Example 1 but in Step D the product obtained in preparation A is used.

EXAMPLE 14

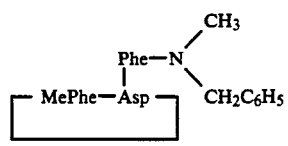

Mass spectrum (FAB):MH+:m/e=527 (molecular weight: 526.6)

EXAMPLE 15

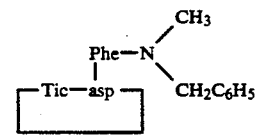

Mass spectrum (FAB):MH+:m/e=525 (molecular weight: 524.6)

EXAMPLE 16

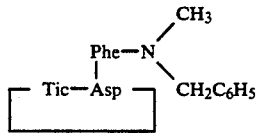

Mass spectrum (FAB):MH+:m/e=525 (molecular weight: 524.6)

EXAMPLE 17

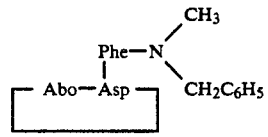

Mass spectrum (FAB):MH+:m/e=503 (molecular weight: 502.6)

EXAMPLE 18

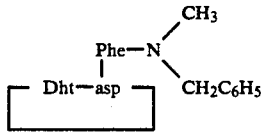

Mass spectrum (FAB):MH+:m/e=557 (molecular weight: 556)

EXAMPLE 19

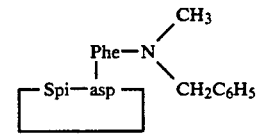

EXAMPLE 20

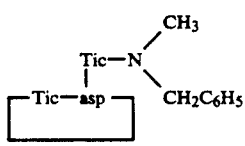

Compound obtained like in preparation A, using Boc-Phe-OH instead of Boc-Tic-OH

EXAMPLE 21

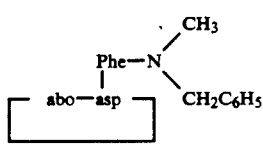

Mass spectrum (FAB):MH+:m/e=503 (molecular weight: 502.6)

EXAMPLE 22

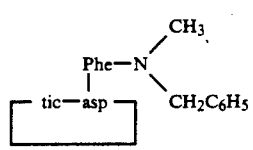

EXAMPLE 23

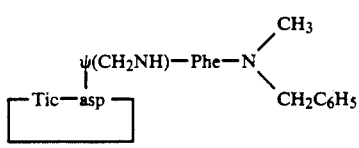

EXAMPLE 24

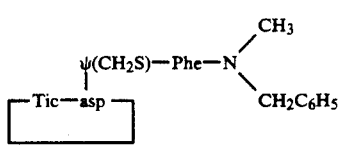

The following examples are obtained using synthesis of example 1.

EXAMPLE 25

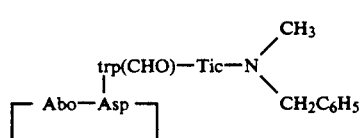

Mass spectrum (FAB):MH+:m/e=729 (molecular weight: 728.8)

EXAMPLE 26

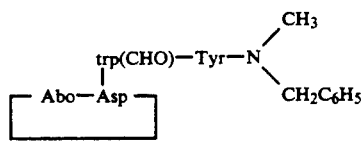

Mass spectrum (FAB):MH+:m/e=733 (molecular weight: 732.8)

EXAMPLE 27

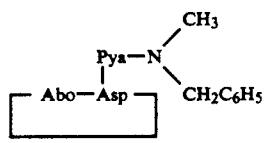

Mass spectrum (FAB):MH+:m/e=604 (molecular weight: 503.6)

EXAMPLE 28

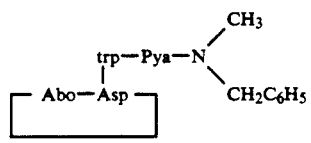

Mass spectrum (FAB): MH+: m/e=690 (molecular weight: 689.8)

EXAMPLE 29

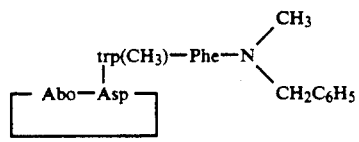

Mass spectrum (FAB): MH+: m/e=703 (molecular weight: 702)

EXAMPLE 30

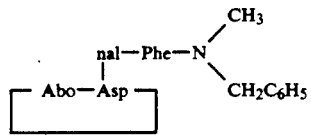

Compound synthesized in an identical manner to Example 1, the compound of preparation B being obtained starting from Boc-nal-OH.

Mass spectrum (FAB): MH+ m/e=700 (molecular weight: 699.85)

EXAMPLE 31

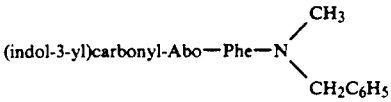

Step A

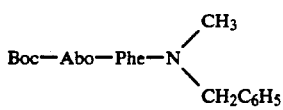

To a solution containing 3.3 mmol of the compound obtained in preparation A (in the form of hydrochloride) and 3.3 mmol of triethylamine in 35 ml of dimethylformamide are added 3.3 mmol of Boc-Abo-OH, 3.3 mmol of HOBT and 3.6 mmol of DCC. The mixture is kept stirred for 18 hours. The expected product is isolated proceeding as in preparation A and purified by chromatography on a silica column using as solvent for elution ethyl acetate.

Yield: 83%

Step B

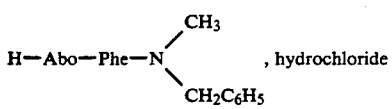

2.8 mmol of the product obtained in Step A are introduced into a 3.2N hydrochloric acid solution in ethyl acetate. The whole is kept stirred at room temperature for one hour, then concentrated in vacuo. The residue is taken up with ether. The expected product precipitates, and is filtered, washed with ether and dried.

Yield: 54%

Step C

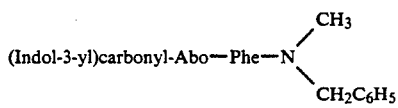

To a solution containing 1.13 mmol of the compound obtained in the preceding step and 1.13 mmol of triethylamine in 12 ml of dimethylformamide are added successively 1.13 mmol of 3-indolecarboxylic acid, 1.13 mmol of HOBT and 1.24 mmol of DCC. The mixture is kept stirred for 24 hours. The expected product is obtained proceeding as in preparation A and is purified by chromatography.

Yield: 23%

Mass spectrum (FAB): MH+: m/e=549 (molecular weight: 548.7)

The following examples were obtained using the same synthesis procedure as that described in Example 24.

EXAMPLE 32

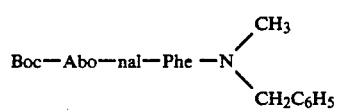

Mass spectrum (FAB): MH+: m/e=703 (molecular weight: 702.9)

EXAMPLE 33

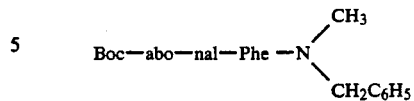

Mass spectrum (FAB): MH+: m/e=703 (molecular weight: 702.9)

EXAMPLE 34

H-Trp-ψ(CH2S)-Phe-Abo-Phe-NH2

The three following examples were obtained using the solid phase synthesis procedure, according to Erickson and Merrifield.

EXAMPLE 35

H-Trp-Phe-Abo-Phe-NH2.CF3CO2H

Mass spectrum (FAB): MH+: m/e=635 (molecular weight, free base: 634.8)

EXAMPLE 36

Z-Phe-abo-Trp-NH2

Mass spectrum (FAB): MH+: m/e=622 (molecular weight: 621.7)

EXAMPLE 37

Benzhydrylcarbonyl-Abo-Leu-Trp-NH2

Mass spectrum (FAB): MH+: m/e=648 (molecular weight: 647.8)

EXAMPLE 38

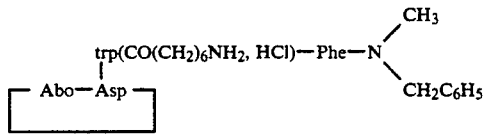

Step A: Boc-NH-(CH2)5-COOH 5 g (34.4 mmol) of 7-aminoheptanoic acid are dissolved in 80 ml of a dioxane/water mixture (45:35). 34.4 ml of 1N sodium hydroxide are added at 0° C. 8.27 g (37.84 mmol) of di-tert-butyl dicarbonate previously dissolved in 25 ml of dioxane are added dropwise. After stirring overnight and acidification to pH 2 with a 15% potassium hydrogen sulfate solution, the organic phase, after customary treatment, yields a yellow gel, precipitating in white powder form (8.40 g) in an ether/pentane mixture.

Yield: 100%

Step B: Boc-NH-(CH2)6-COO-Np

Where Np stands for paranitrophenyle group.

To 3 g (12.2 mmol) of compound obtained in Step A in 10 ml of dichloromethane are added 1.874 g (13.4 mmol) of para-nitrophenol, and then 2.775 g (13.5 mmol) of DCC. After stirring for 2 days sheltered from the light, the urea formed in the course of the reaction is removed by filtration. Treatment with pentane of the concentrated organic phase yields 3.23 g of a pale yellow precipitate.

Yield: 72%

Step C

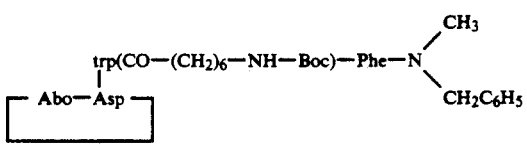

To 0.959 g (3.63 mmol) of 18-6 crown ether in 40 ml of tetrahydrofuran are added 2.5 g (3.63 mmol) of compound obtained in Example 33, 1.662 g (4.54 mmol) of the compound obtained in Step B and 791 μl (4.54 mmol) of diisopropylethylamine and 422 mg of potassium fluoride. The mixture is left stirring for 70 hours sheltered from the light and is then concentrated in vacuo. The reaction medium is taken up with an ether-/ethyl acetate mixture and then, after customary treatment of the organic phase and taking up in ether, an off-white product precipitates. The latter is purified by chromatography on silica (eluent chloroform/methanol 97:3) to give 1.59 g of expected product in white crystalline form.

Yield: 47% Step D

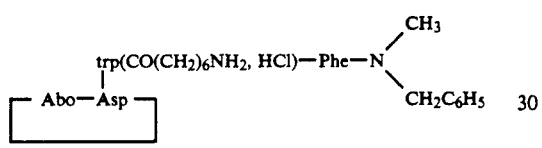

1.5 g (1.64 mmol) of protected peptide obtained in Step C are dissolved in 100 ml of an ethyl acetate solution saturated with gaseous hydrochloric acid. After stirring for 1 h 30 at room temperature, evaporation of the solvent, precipitation in ether and purification by inverted phase preparative HPLC and on an anion exchange resin colum (Amberlite IRA-93) followed by chlorhydrate formation, 723 mg of off-white powder corresponding to the expected product are obtained.

Yield: 52%

The two following examples have been carried out using the same synthesis process as that described for Example 38.

EXAMPLE 39

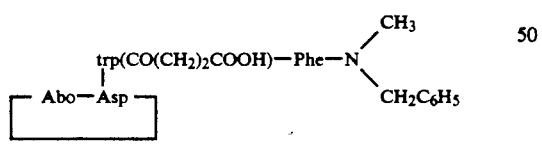

Mass spectrum (FAB): MH+: m/e=789 (molecular weight: 788.9)

EXAMPLE 40

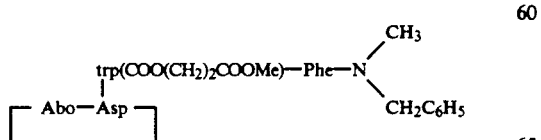

Mass spectrum (FAB): MH+: m/e=803 (molecular weight: 802.9) Compounds of examples 41 of 46 were prepared as that of example 38 with the following modifications:

solvent: CH2Cl2 (instead of THF)
crushed sodium hydroxyde (instead of crowm-ether and potassium fluoride)
acylating agent: acylchloride (instead of active ester or anhydride) in the presence of phase transfer catalyst- :tetrabutyl ammonium bisulfate.

EXAMPLE 41

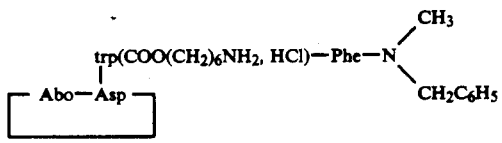

Mass spectrum (FAB): MH+: m/e=832 (molecular weight: 832.0)

EXAMPLE 42

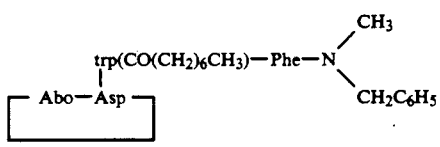

To the compound obtained in Example 9 dissolved in methylene chloride are added n-octanoyl chloride, finely crushed sodium hydroxide and tetrabutylammonium hydrogenosulfate, to lead to the expected product.

Mass spectrum (FAB): MH+: m/e=815 (molecular weight: 815)

The following examples have been carried out using the same synthesis process as that described for Example 42.

EXAMPLE 43

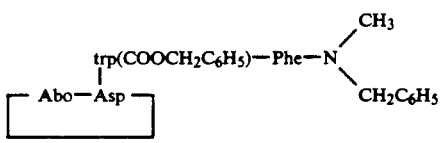

Mass spectrum (FAB): MH+: m/e=823 (molecular weight: 822)

EXAMPLE 44

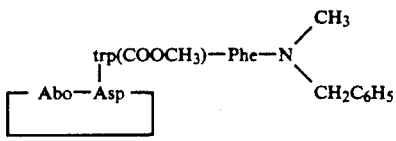

Mass spectrum (FAB): MH+: m/e=823 (molecular weight: 822)

EXAMPLE 45

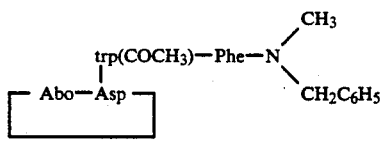

Mass spectrum (FAB): MH+: m/e=731 (molecular weight: 730)

EXAMPLE 46

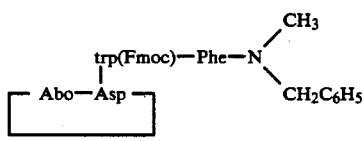

Mass spectrum (FAB): MH+: m/e=911 (molecular weight: 911.1)

PHARMACOLOGICAL STUDY OF THE DERIVATIVES OF THE INVENTION

EXAMPLE 47

Bio assays on isolated smooth muscle

In order to evaluate the neurokinin antagonistic potential of the compounds of the invention, three smooth muscle preparations were used. Each of these preparations, described as having a good specificity for one type of receptor for neurokinins, was carried out conforming to the following techniques described in the literature:

rabbit vena cava for the study of the $NK_1$ receptor according to D. REGOLI et al. (J. Cardiovasc. Pharmacol., in press);

rabbit pulmonary artery without endothelium for the study of the $NK_2$ receptor according to D. REGOLI et al. (European J. Pharmacol. 125, 37–44, 1985);

rat portal vein for the study of the $NK_3$ receptor according to D. REGOLI et al. (European J. Pharmacol. 134, 321-326, 1986).

The antagonistic power of the compounds of the invention is expressed in the form of $pA_2$ as defined by O. ARUNLAKSHANA and H. O. SCHILD (Brit. J. Pharmacol., 14, 48–58, 1959).

| BRIEF IDENTIFICATION OF EXAMPLES | |
|---|---|
| Seq ID N° 1: | Cyclo(Abo—Asp)—trp(CHO)—Phe—N(CH$_3$)CH$_2$C$_6$H$_5$ |
| Seq ID N° 2: | Cyclo(abo—Asp)—trp(CHO)—Phe—N(CH$_3$)CH$_2$C$_6$H$_5$ |
| Seq ID N° 3: | Cyclo(Tic—Asp)—trp(CHO)—Phe—N(CH$_3$)CH$_2$C$_6$H$_5$ |
| Seq ID N° 4: | Cyclo(Abo—asp)—trp(CHO)—Phe—N(CH$_3$)CH$_2$C$_6$H$_5$ |
| Seq ID N° 5: | Cyclo(abo—asp)—trp(CHO)—Phe—N(CH$_3$)CH$_2$C$_6$H$_5$ |
| Seq ID N° 6: | Cyclo(Tic—asp)—trp(CHO)—Phe—N(CH$_3$)CH$_2$C$_6$H$_5$ |
| Seq ID N° 7: | Cyclo(MePhe—Asp)—trp(CHO)—Phe—N(CH$_3$)CH$_2$C$_6$H$_5$ |
| Seq ID N° 8: | Cyclo(Arg(NO$_2$)—Asp)—trp(CHO)—Phe—N(CH$_3$)CH$_2$C$_6$H$_5$ |
| Seq ID N° 9: | Cyclo(Abo—Asp)—trp—Phe—N(CH$_3$)CH$_2$C$_6$H$_5$ |
| Seq ID N° 10: | Cyclo(Abo—Asp)—trp(COOtBu)—Phe—N(CH$_3$)CH$_2$C$_6$H$_5$ |
| Seq ID N° 11: | Cyclo(abo—asp)—trp—Phe—N(CH$_3$)CH$_2$C$_6$H$_5$ |
| Seq Id N° 12: | Cyclo(hyp—asp)—trp(CHO)—Phe—N(CH$_3$)CH$_2$C$_6$H$_5$ |
| Seq ID N° 13: | Cyclo(Hyp—Asp)—trp(CHO)—Phe—N(CH$_3$)CH$_2$C$_6$H$_5$ |
| Seq ID N° 14: | Cyclo(MePhe—Asp)—Phe—N(CH$_3$)CH$_2$C$_6$H$_5$ |
| Seq ID N° 15: | Cyclo(Tic—asp)—Phe—N(CH$_3$)CH$_2$C$_6$H$_5$ |
| Seq ID N° 16: | Cyclo(Tic—Asp)—Phe—N(CH$_3$)CH$_2$C$_6$H$_5$ |
| Seq ID N° 17: | Cyclo(Abo—Asp)—Phe—N(CH$_3$)CH$_2$C$_6$H$_5$ |
| Seq ID N° 18: | Cyclo(Dht—asp)—Phe—N(CH$_3$)CH$_2$C$_6$H$_5$ |
| Seq ID N° 19: | Cyclo(Spi—asp)—Phe—N(CH$_3$)CH$_2$C$_6$H$_5$ |
| Seq ID N° 20: | Cyclo(Tic—asp)—Tic—N(CH$_3$)CH$_2$C$_6$H$_5$ |
| Seq ID N° 21: | Cyclo(abo—asp)—Phe—N(CH$_3$)CH$_2$C$_6$H$_5$ |
| Seq ID N° 22: | Cyclo(tic—asp)—Phe—N(CH$_3$)CH$_2$C$_6$H$_5$ |
| Seq ID N° 23: | Cyclo(Tic—asp)—Ψ(CH$_2$NH)—Phe—N(CH$_3$)CH$_2$C$_6$H$_5$ |
| Seq ID N° 24: | Cyclo(Tic—asp)—Ψ(CH$_2$S)—Phe—N(CH$_3$)CH$_2$C$_6$H$_5$ |
| Seq ID N° 25: | Cyclo(Abo—Asp)—trp(CHO)—Tic—N(CH$_3$)CH$_2$C$_6$H$_5$ |
| Seq ID N° 26: | Cyclo(Abo—Asp)—trp(CHO)—Tyr—N(CH$_3$)CH$_2$C$_6$H$_5$ |
| Seq ID N° 27: | Cyclo(Abo—Asp)—Pya—N(CH$_3$)CH$_2$C$_6$H$_5$ |
| Seq ID N° 28: | Cyclo(Abo—Asp)—trp—Pya—N(CH$_3$)CH$_2$C$_6$H$_5$ |
| Seq ID N° 29: | Cyclo(Abo—Asp)—trp(CH$_3$)—Phe—N(CH$_3$)CH$_2$C$_6$H$_5$ |
| Seq ID N° 30: | Cyclo(Abo—Asp)—nal—Phe—N(CH$_3$)CH$_2$C$_6$H$_5$ |
| Seq ID N° 31: | (indol-3-yl) carbonyl—Abo—Phe—N(CH$_3$)CH$_2$C$_6$H$_5$ |
| Seq ID N° 32: | Boc—Abo—nal—Phe—N(CH$_3$)CH$_2$C$_6$H$_5$ |
| Seq ID N° 33: | Boc—abo—nal—Phe—N(CH$_3$)CH$_2$C$_6$H$_5$ |
| Seq ID N° 34: | H—trp—Ψ(CH$_2$S)—Phe—Abo—Phe—NH$_2$ |
| Seq ID N° 35: | H—trp—Phe—Abo—Phe—NH$_2$, CF$_3$CO$_2$H |
| Seq ID N° 36: | Z—Phe—abo—trp—NH$_2$ |
| Seq ID N° 37: | Benzhydryl carbonyl—Abo—Leu—Trp—NH$_2$ |
| Seq ID N° 38: | Cyclo(Abo—Asp)—trp(CO(CH$_2$)$_6$NH$_2$, HCl)—Phe—N(CH$_3$)CH$_2$C$_6$H$_5$ |
| Seq ID N° 39: | Cyclo(Abo—Asp)—trp(CO(CH$_2$)$_2$COOH)—Phe—N(CH$_3$)CH$_2$C$_6$H$_5$ |
| Seq ID N° 40: | Cyclo(Abo—Asp)—trp(COO(CH$_2$)$_2$COOMe)—Phe—N(CH$_3$)CH$_2$C$_6$H$_5$ |
| Seq ID N° 41: | Cyclo(Abo—Asp)—trp(COO(CH$_2$)$_6$NH$_2$, HCl)—Phe—N(CH$_3$)CH$_2$C$_6$H$_5$ |
| Seq ID N° 42: | Cyclo(Abo—Asp)—trp(CO(CH$_2$)$_6$CH$_3$)—Phe—N(CH$_3$)CH$_2$C$_6$H$_5$ |
| Seq ID N° 43: | Cyclo(Abo—Asp)—trp(COOCH$_2$C$_6$H$_5$)—Phe—N(CH$_3$)CH$_2$C$_6$H$_5$ |
| Seq ID N° 44: | Cyclo(Abo—Asp)—trp(COOCH$_3$)—Phe—N(CH$_3$)CH$_2$C$_6$H$_5$ |
| Seq ID N° 45: | Cyclo(Abo—Asp)—trp(COCH$_3$)—Phe—N(CH$_3$)CH$_2$C$_6$H$_5$ |
| Seq ID N° 46: | Cyclo(Abo—Asp)—trp(Fmoc)—Phe—N(CH$_3$)CH$_2$C$_6$H$_5$ |

The results as non limitative examples are assembled in the table below.

| EXAMPLE | pA$_2$ | | |
|---|---|---|---|
| | NK$_1$ | NK$_2$ | NK$_3$ |
| 1 | 6.46 | 4.86 | 4.86 |
| 5 | 7.16 | 5.70 | 4.86 |
| 6 | 6.87 | <5.17 | 4.87 |
| 7 | 6.87 | 4.87 | 4.87 |
| 9 | 7.00 | 6.00 | 5.80 |
| 16 | 6.02 | 4.72 | 4.72 |
| 31 | 7.34 | 4.86 | 5.04 |
| 38 | 6.70 | 4.70 | 5.70 |

The compounds of the invention have a powerful antagonistic activity with respect to NK$_1$ receptors, with, for the most part, a lower activity for the NK$_2$ and NK$_3$ receptors.

This is more particularly the case for the compound of Example 24.

EXAMPLE 48

In vivo activity. Eddy test in the mouse.

Because of the involvement of substance P in the transmission of pain at the spinal level (M. OTSUKA and S. KONISHI, TINS, 6, 317–320, 1983), the in vivo pharmacological activity of the compounds of the invention was studied in the mouse in the thermal hyperalgesia test initially described by N. B. EDDY et al. (J. Pharmacol. Exp. Ther., 107, 385–393, 1953). This test consists in measuring the reaction time to heat determined by licking of the forepaws in a mouse (CD$_1$ male, Ch. River, 25–30 g) placed on a metal plate heated to 55° C.

The animals were treated intravenously with the compounds of the invention 5 minutes before passing onto the heating plate.

The mean of the reaction times obtained for each batch treated (12 mice per batch) was compared with the mean of the corresponding control batch. The results are expressed in the form of the ED$_{50}$ which corresponds to the dose increasing the reaction time by 50%.

These results are assembled in the table below.

| EXAMPLE | Eddy test in the mouse ED$_{50}$ (mg/kg i.v.) |
|---|---|
| 1 | 0.2 |
| 5 | 3.5 |
| 6 | 3.0 |
| 7 | 4.0 |
| 9 | 0.5 |
| 16 | 3.0 |
| 31 | 4.0 |
| 38 | 2.0 |
| morphine | 0.5 |

The compounds of the invention have considerable analgesic properties. The compound of Example 1 more particularly has an analgesic power superior to that of morphine.

The antalgic activity of the compounds of the invention which may act on any neurokinin receptor different from those known, is also claimed.

PHARMACEUTICAL COMPOSITION

EXAMPLE 49

Tablets: Preparation formula for 1,000 2 mg tablets

| Compound of Example 1 | 2 g |
|---|---|
| Hydroxypropylcellulose | 2 g |
| Wheat starch | 10 g |
| Lactose | 100 g |
| Magnesium stearate | 3 g |
| Talc | 3 g |

We claim:
1. A compound selected from those of formula (I):

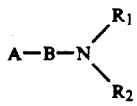

in which:
R₁ is methyl and R₂ is benzyl,
B represents a residue of an aromatic amino acid,
A represents
either a peptide residue of formula:

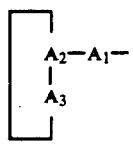

in which:
A₁ represents a bond, a residue 2-azabicyclo[2.2.2]octane-3-carbonyl (Abo), leucine (Leu), β-naphthylalanine (Nal), tryptophan (Trp) or tryptophan protected by Q (Trp(Q)),
Q representing the radical

in which
X represents a bond, —CO— or —COO—,
n is an integer from 0 to 10,
R' is hydrogen, linear or branched ($C_1$–$C_{10}$) alkyl, benzyl, 9-fluorenylmethyl, —NH₂, —COOH or —COOR" (R"=linear or branched ($C_1$–$C_8$) alkyl),
A₂ represents an aspartic acid residue (Asp) or glutamic acid residue (Glu),
A₃ represents a residue 1,2,3,4-tetrahydroisoquinoline-3-carbonyl (Tic), 2-azabicyclo[2.2.2]octane-3-carbonyl (Abo), methylphenylalanine (MePhe), arginine (Arg), arginine protected by nitro (Arg (NO₂)), 6,7-dihydroxy-1,2,3,4-tetrahydroisoquinoline (Dht), spinacine (Spi), 4-hydroxyproline (Hyp), β-naphthylalanine (Nal) or proline (Pro),
it being understood that the peptide bond (—CO—NH—) between A₁ and A₂ or between A₂ and B in the case where A₁ is a bond, can be replaced by a pseudopeptide bond chosen from amongst —CH₂—NH— and —CH₂—S—, its and epimers as well as its pharmaceutically-acceptable acid or base addition salts, it being understood that each amino acid of the peptide sequence is optically pure and that the α carbon of each amino acid can be of D or L configuration.

2. A compound as claimed in claim 1 in which B represents a residue phenylalanine (Phe), tyrosine (Tyr) 1,2,3,4-tetrahydroisoquinoline-3-carbonyl (Tic), tryptophan (Trp) or tryptophan protected by formyl (Trp (CHO)), 3-pyridinylalanine (Pya), its as well as its pharmaceutically-acceptable acid or base addition salts.

3. A compound as claimed in claim 1 which is selected from

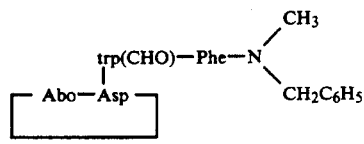

and its.

4. A compound which is selected from

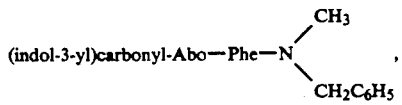

and its.

5. A compound as claimed in claim 1 which is selected from

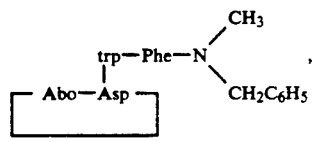

and its.

6. A compound as claimed in claim 1 which is selected from

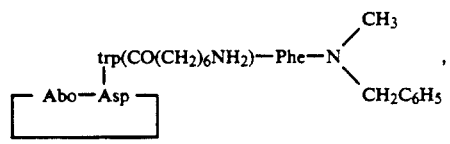

and its as well as its ammonium salts.

7. A compound as claimed in claim 1 which is selected from

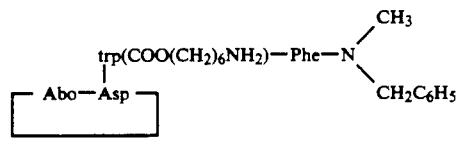

and its as well as its ammonium salts.

8. A method for treating an animal or human living body afflicted with a disease requiring an antagonist of substance P, which substance leads to pain, inflammation, gastrointestinal disorders, asthma, allergies and disorders of the central nervous system, which comprises the step of administering to said living body an amount of a compound of claim 1 which is effective for alleviation of said disease.

9. A pharmaceutical composition useful in which contains as active ingredient an effective amount of a compound according to claim 1, on its own or in combination with one or more pharmaceutically-acceptable excipients or vehicles.

* * * * *

UNITED STATES PATENT AND TRADEMARK OFFICE
CERTIFICATE OF CORRECTION

PATENT NO. : 5,317,014

DATED : May 31, 1994

INVENTOR(S) : Jean-Luc Fauchere, Nathalie Kucharczyk, Angela D. Morris, Joseph Paladino, Jacqueline Bonnet, Christophe Thurieau It is certified that error appears in the above-indentified patent and that said Letters Patent is hereby corrected as shown below:

Col. 2, line 17,
TITLE PAGE, Assistant Examiner; "Sabata" should read --Salata--
Column 41, line; / "CycloAbo" should read --Cyclo-Abo--
Column 55, line 10; delete "either"
Column 55, line 48; "—CH-" should read -- —CH$_2$ --
Column 55, line 49; delete "$_2$" first occurrence and delete "its and epimers"
Column 55, line 59; delete "its" first occurrence
Column 55, line 61&62 delete "selected from"
Column 56, line 9; delete "and its"
Column 56, line 10; delete "selected from"
Column 56, line 16; delete "and its"
Column 56, line 17& 18; delete "selected from"
Column 56, line 27; delete "and its"
Column 56, line 38; delete "and its"
Column 56, line 48; delete "and its"
Column 56, line 57; delete "useful in"

Signed and Sealed this

First Day of November, 1994

Attest:

Attesting Officer

BRUCE LEHMAN

Commissioner of Patents and Trademarks